United States Patent [19]

Nakata et al.

[11] Patent Number: 5,083,869

[45] Date of Patent: Jan. 28, 1992

[54] PHOTOCOUSTIC SIGNAL DETECTING DEVICE

[75] Inventors: Toshihiko Nakata; Yukio Kembo, both of Yokohama, Japan

[73] Assignee: Hitachi, Ltd., Tokyo, Japan

[21] Appl. No.: 384,541

[22] Filed: Jul. 24, 1989

[30] Foreign Application Priority Data

Jul. 27, 1988 [JP] Japan .............................. 63-185597

[51] Int. Cl.$^5$ ............................................. G01N 21/00
[52] U.S. Cl. ..................................... 356/432; 356/358
[58] Field of Search ................... 356/123, 432, 432 T, 356/358

[56] References Cited

U.S. PATENT DOCUMENTS

| 3,912,922 | 10/1975 | Lacotte et al. | |
|---|---|---|---|
| 4,046,477 | 9/1977 | Kaule | 356/358 |
| 4,243,327 | 1/1981 | Frosch et al. | 356/432 |
| 4,350,410 | 9/1982 | Minott | 350/170 |
| 4,633,715 | 1/1987 | Monchalin | 356/358 |
| 4,854,710 | 8/1989 | Opsal et al. | 356/432 |

FOREIGN PATENT DOCUMENTS

| 0163466 | 4/1985 | European Pat. Off. | |
|---|---|---|---|
| 2704 | 1/1979 | Japan | 356/123 |
| 1185953 | 4/1970 | United Kingdom | 356/111 |

OTHER PUBLICATIONS

H. I. Ringermacher, et al., "Laser-In/Laser-Out Photoacoustics Using Doppler Heterodyne Interferometry", IEEE Ultrasonics Symposium Proceedings, Nov. 1986, vol. 1, pp. 407–410 (English).
G. S. Kino, et al., "Optical Measurements of Acoustic and Photoacoustic Effects", IEEE Ultrasonics Symposium Proceedings, Nov. 1986, vol. 1, pp. 505–514 (English).
K. F. Etzold, "Transducer Characterization by Interferometry", IEEE Ultrasonics Symposium, Oct. 1982, vol. 2, pp. 867–870.
M. Hangyo et al., "Photoacoustic Microscope", from Hihakai Kensa, vol. 36, No. 10, Oct. 1987, pp. 730–736 (No English translation available to applicants' attorney).
P. Cielo, et al., "Laser Generation of Convergent Acoustic Waves and Applications to Materials Evaluation", from IEEE Ultrasonics Symposium, 1986, pp. 515–526.

Primary Examiner—Richard A. Rosenberger
Attorney, Agent, or Firm—Fay, Sharpe, Beall, Fagan, Minnich & McKee

[57] ABSTRACT

A photoacoustic signal detecting device irradiates a modulated light on a sample using focusing means, detects a photoacoustic signal created in the sample using light interference detection means and finally displays the information relative to the surface and inside of the sample. The focusing means and light interference detection means are constructed in a confocal optical system, respectively, and a pin-hole is used to remove unnecessary high order diffraction light components around the light spot of the modulated light so that the photoacoustic signal can be detected with a high accuracy. Further, an auto-focusing function is added to the photoacoustic signal detection so that the photoacoustic signal can be detected with a high accuracy also for a sample with rugged surface.

14 Claims, 5 Drawing Sheets

PHOTOCOUSTIC SIGNAL DETECTING DEVICE

BACKGROUND OF THE INVENTION

The present invention relates to a photoacoustic signal detecting device for detecting information relative to the surface and inside of a sample using photoacoustic effect.

The photoacoustic effect, which was discovered by Tyndall, Bell, Röntgen, et al. in 1881, represents the following phenomenon. When intensity-modulated light (intermittent light) is irradiated to a sample, heat is generated in a light absorption region and periodically diffused through a heat diffusion region so that the thermal distortion wave thus generated provides an ultrasonic wave. By detecting this ultrasonic wave i.e. a photoacoustic wave by a microphone (acoustic-electric converter) or a piezoelectric element to obtain the component in synchronism with the incident light, information relative to the surface and inside of the sample can be obtained. Particularly, by varying the modulation frequency, information in the depth direction of the sample can be obtained. A technique for detecting the above photoacoustic signal is disclosed in "HIHAKAI KENSA", Vol. 36, No. 10, pp. 730–736, October 1987 (Showa 62). However, this technique has the following problem in view of detecting the internal information of a sample in a non-contact non-destruction manner. In the system of using a microphone, in order to enhance the measurement sensitivity, the measurement must be carried out under the state that a sample is placed in a sealed chamber with the size of generally several cm's or so. Thus, the sample size will be limited to 1 to 2 cm. As the case may be, the sample must be cut. In the case of using a piezoelectric element, the piezoelectric element must be bonded to the back surface of a sample. Thus, the detecting sensitivity will be greatly varied according to the contact degree.

Then, a system of using light interference has lately attracted considerable attention as a technique of detecting a photoacoustic signal. This system is discussed in IEEE; 1986 ULTRASONIC SYMPOSIUM—pp. 515–526 (1986). Now referring to FIG. 7, a system using light interference will be explained in the case where a laser is used as a light source.

Figure 7:
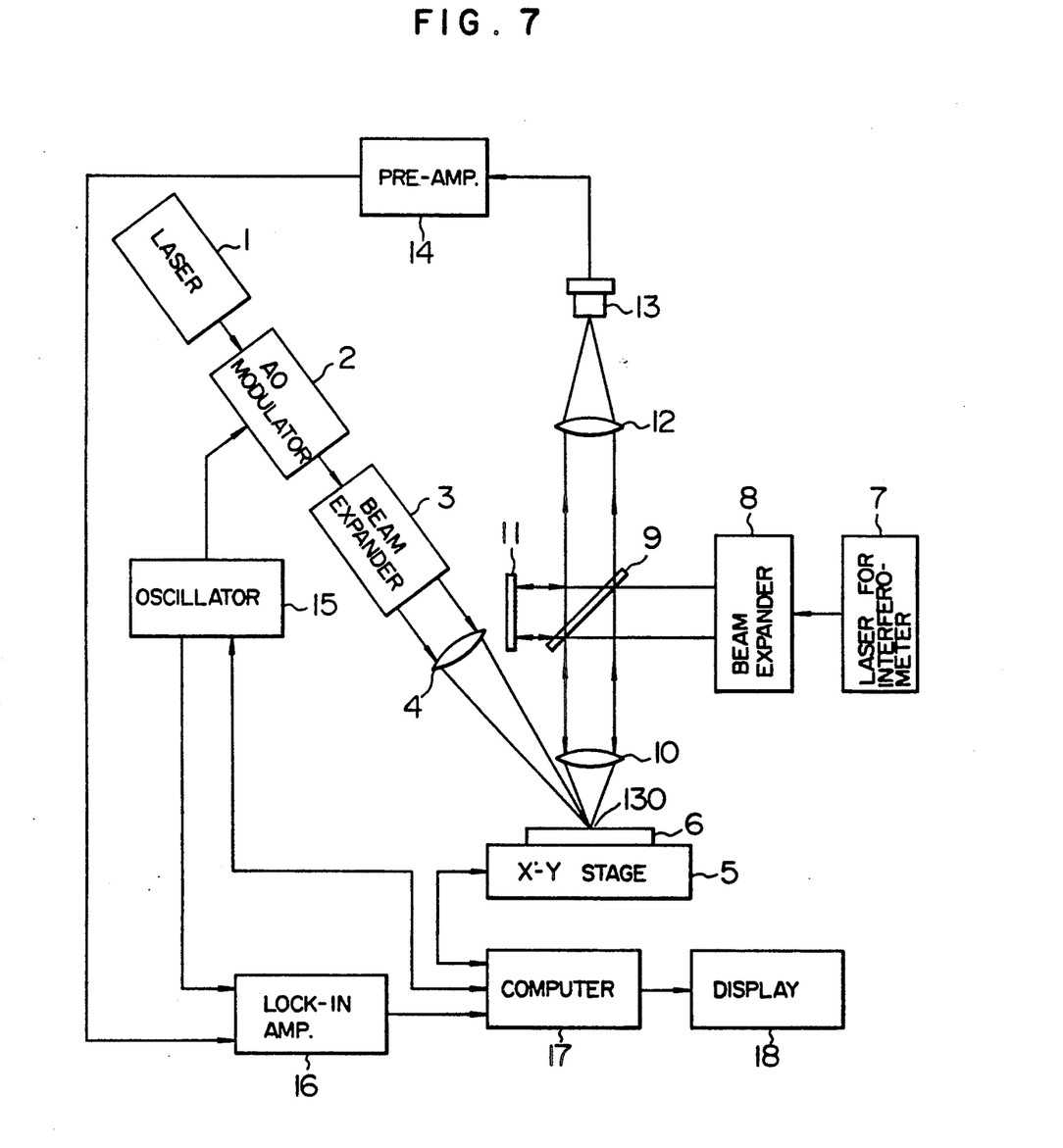
FIG. 7 is a block diagram showing a photoacoustic signal detecting device (optical system)

A parallel light emitted from a laser 1 is intensity-modulated an acoustic-optical modulation element (AO converter) 2. The thus obtained intermittent light is expanded to a beam of a desired diameter by a beam expander, which is thereafter focused on the surface of a sample 6 placed on an XY stage 5 by a lens 4. Then, the heat distortion wave created at a focusing position 130 generates an ultrasonic wave and also provides a minute displacement in the sample surface. This minute displacement will be detected by a Michelson interferometer explained below. A parallel light emitted from a laser 7 is expanded to a beam of a desired diameter by a beam expander 8. This beam is separated into two optical paths by a beam splitter 9. The one is focused on the focusing position 130 on the sample 6 by a lens 10 whereas the other is irradiated to a reference mirror 11. Then, the light reflected from the sample 6 and the light reflected from the reference mirror 11 interfere with each other. The interference pattern thus formed is focused on a photo-electric converting element 13 (e.g. photodiode) through a lens 12 to provide a photo-electric-converted interference intensity signal. This interference intensity signal is amplified by a preamplifier 14 and thereafter sent to a lock-in amplifier 16. The lock-in amplifier 16, using as a reference signal a modulated frequency signal from an oscillator 15 used for driving the acoustic-optical modulation element 2, extracts only the modulated frequency component contained in the interference intensity signal. This frequency component has information relative to the surface or inside of the sample according to the frequency. Therefore, if there is a defect such as a crack inside the sample, the modulated frequency component in the interference intensity signal provides a signal change so that the presence of the defect can be noticed. An XY stage shifting signal and an output signal from the lock-in amplifier 16 are processed by a computer 17. Accordingly, the photoacoustic signals corresponding to the respective positions on the sample are displayed on a display (e.g. a monitor television) 18 as image information.

The above mentioned prior art using light interference is a very efficient technique in that it enables a photoacoustic signal to be detected in a non-contact and non-destruction manner, but also has the following problem.

The transverse resolution of the photoacoustic signal is decided by the spot diameter on the sample of the laser beam from the laser 1 and the heat diffusion length of the sample. The heat diffusion length is a value peculiar to the sample whereas the spot diameter d is expressed by $$d = 1.22 \lambda f/D \qquad (1)$$

where $\lambda$ is the wavelength of the laser beam, D is the beam diameter after having passed the beam expander, and f is the focal length of the lens 4.

Figure 8:
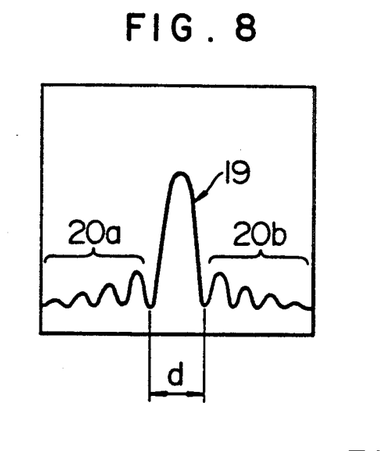
FIG. 8 is a view showing the light intensity distribution of a laser spot.

However, generally, the light intensity distribution of the beam spot on the sample 6 has a sectional shape as shown in FIG. 8. Namely, there are high order diffraction components 20a and 20b around a peak portion having the diameter of d. Generally, the light intensity of the high order diffraction components is as high as 16.2% in that of the entire spot. If a minute displacement on the sample surface is detected through light interference, this value can not disregarded so that the transverse resolution of the photoacoustic signal is finally reduced. This applies to the spot diameter of the laser beam from the laser 7 for an interferometer. Namely, the transverse resolution of the interference intensity signal is reduced. Particularly, the reflection light of the high order diffraction component, when being incident to the photo-electric converting element 13, provides noise, which greatly reduces the detection sensitivity of the photoacoustic signal.

SUMMARY OF THE INVENTION

An object of the present invention is to provide a photoacoustic signal detecting device which can measure information relative to the surface and inside of a sample with a high accuracy by improving the detecting sensitivity of a photoacoustic signal.

In accordance with the present invention, there is provided a photoacoustic signal detecting device comprising a light source, modulation means for intensity-modulating the light emitted from the light source at a desired frequency, focusing means for focusing the modulated light on a sample, light interference detecting means for detecting a light interference signal due to the photoacoustic effect generated in the sample through light interference, and extraction means for extracting the information relative to the surface and inside of the sample form the light interference signal detected by the light interference detecting means. The focusing means and the light interference detecting means are constructed in a common focal point optical system.

By arranging a pin-hole at the focal point of the common focal point optical system of the above focusing means, unnecessary high order diffraction components around the peak position of a beam spot on the sample are removed so that the transverse resolution, detecting sensitivity and S/N of a photoacoustic signal can be improved. Likewise, by arranging a pin-hole at the common focal point system of the light interference detecting means, the same effect can be obtained for an interference intensity signal.

Further, by adding an auto-focusing function to the photoacoustic signal detecting device in accordance with the present invention, the sample or the focusing means can be adjusted so that the diameter of the beam spot focused on the sample is always constant. By means of this auto-focusing function, the irradiation power of light emitted from the light source is made constant also for the sample with a rugged surface. As a result, a stabilized photoacoustic signal can be obtained so that the transverse resolution, detecting sensitivity and S/N thereof can be improved.

DESCRIPTION OF THE PREFERRED EMBODIMENTS

Now referring to FIGS. 1 to 6, embodiments of the present invention will be explained.

Figure 1:
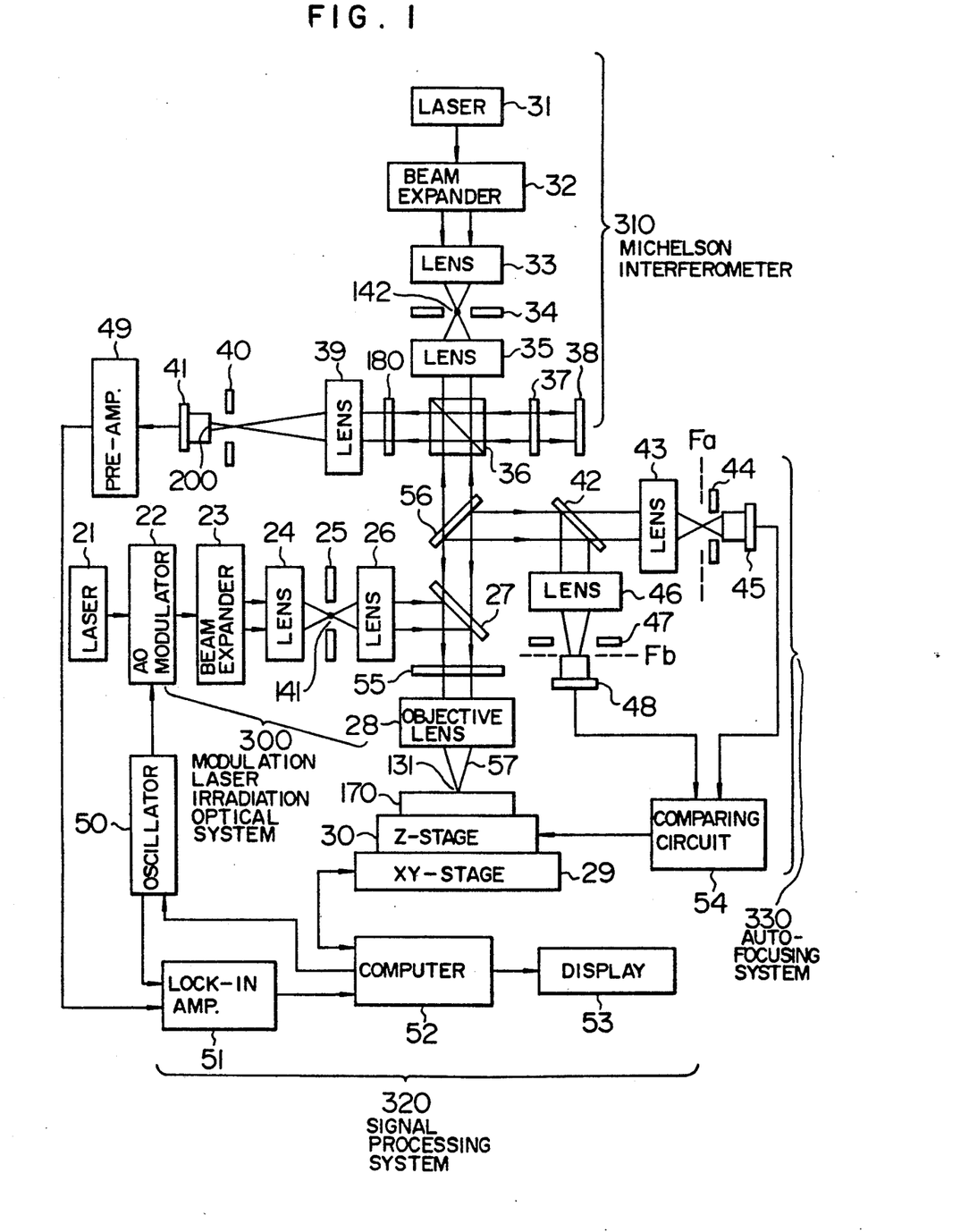
FIG. 1 is a block diagram of the photoacoustic signal detecting device (optical system) in accordance with a first embodiment of the present invention.
Figure 2:
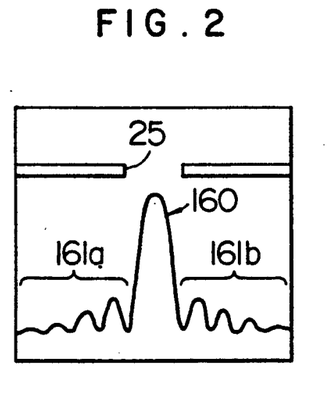
FIG. 2 is a view for explaining the manner of shading the high order diffraction light component of a laser spot through a pin-hole.
Figure 3:
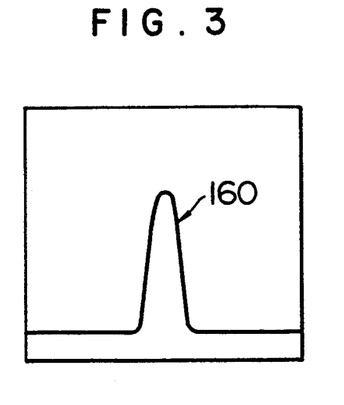
FIG. 3 is a graph showing the light intensity distribution of a laser beam immediately after it has passed the pin-hole.

First, a first embodiment of the present invention will be explained with reference to FIGS. 1 to 6. FIG. 1 shows the photoacoustic detecting optical system in accordance with a first embodiment of the present invention in its block form. This optical system is composed of a modulated laser irradiation optical system 300, a Michelson interferometer 310, a signal processing system 320 and auto-focusing system 330. In operation, a parallel light emitted from a laser 21 is intensity-modulated by an acoustic-electric modulation element 22 at a predetermined frequency. Its intermittent light is expanded to a beam having a desired diameter by a beam expander 23, which is thereafter focused by a lens 24 to its rear focal point 141 thereof. A pin-hole 25, which is provided at the focal point 141, shades the high order diffraction light components 161a and 161b around the peak part 160 of the focused beam spot as shown in FIG. 2. As a result, the light intensity distribution immediately after having passed the pin-hole 25 provides only the peak part 160. Since the focal point 141 is also a front focal point of a lens 26, the light from the pin-hole 25, after having passed the lens 26, becomes a parallel light.

This parallel light, after having been reflected from a dichroic mirror 27, becomes a beam spot having the same light intensity distribution as shown in FIG. 3 again at a front focal point 131 of an objective lens 28, i.e. on a sample 170. Namely, the lens 26 and the objective lens 28 are in a confocal relation. A thermal distortion wave created at the focusing position 131 on the sample 170 generates an ultrasonic wave and also provides a minute displacement on sample surface.

On the other hand, a circularly polarized parallel light emitted from a laser 31 having a different wavelength from the laser 21 is expanded to a beam having a desired diameter by a beam expander 32, which is thereafter focused by a lens 33 to its rear focal point 142 thereof. A pin-hole 34, which is provided at the focal point 142, shades the high order diffraction light components around the peak part of the focused beam spot in the same manner as in FIG. 2. Since the focal point 142 is also a front focal point of a lens 35, the light from the pin-hole 34, after having passed the lens 35, becomes a parallel light.

This parallel light is separated into a P polarized light and an S polarized light. The P polarized light permeates through a polarized light beam splitter 36. And further it passes a dichroic mirror 27 and λ/4 plate 55 to become a circularly polarized light. Thus, the image of the beam spot (light intensity distribution of FIG. 3) after having passed the pin-hole 142 is focused at the point 131 on the sample 171 (the front focal point of the objective lens 28). The S polarized light is reflected from the polarized beam splitter 36 and passes λ/4 plate 37 to become a circularly polarized light which is incident to a reference mirror. The light reflected from the sample 170, which has the minute displacement generated on the sample surface as phase information, passes through the objective lens 28 and the λ/4 plate 55 to become the S polarized light which is reflected from the polarized light beam splitter 36. The light reflected from the reference mirror 38 passes through the λ/4 plate 37 to become the P polarized light which permeates the polarized light beam splitter 36.

Figure 4:
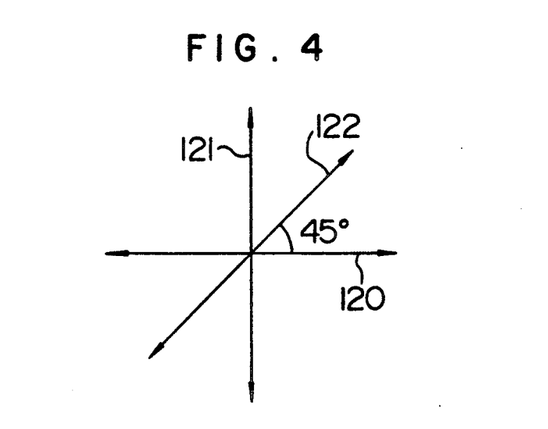
FIG. 4 is a view for explaining the polarization direction in a polarization plate.

In FIG. 4, 120 represents the polarizing direction of the reflection light from the sample 170 and 121 represents that from the reference mirror 38. Since both reflection lights are orthogonal, they do not interfere with each other as they are. However, by inserting a polarization plate 180 into their optical path to place their polarization direction in a direction of 45 degrees, both reflection lights interfere with each other. The interference pattern thus formed, which includes the phase information relative to the minute displacement generated on the sample surface, is focused by a lens 39 at its rear focal point 200 and detected by a photo-electric converting element 41 such as a photodiode. Also, a pin-hole 40 is arranged at the rear focal point 200 in order to shade the stray light created in the objective lens 28, the interference component created in a transparent film on the sample and the high order diffraction light component created due to the minute rugged sample surface.

As understood the above description, in the Michelson interferometer, the lens 35, the objective lens 28 and the lens 39 are in a confocal relation. The photo-electric-converted interference intensity signal is amplified by a pre-amplifier 49 and thereafter sent to a lock-in amplifier 51. The lock-in amplifier 51, using as a reference signal a modulated frequency signal from an oscillator 50 used for driving the acoustic-optical modulation element 22, extracts the modulated frequency component and phase component contained in the interference intensity signal. The frequency component and the phase component have information relative to the surface or inside of the sample according to the frequency. Therefore, if there is a defect such as a crack inside the sample, the modulated frequency component in the interference intensity signal provides a signal change so that the presence of the defect can be noticed. A shifting signal for an XY stage 29 and an output signal from the lock-in amplifier 51 are processed by a computer 52. Accordingly, the photoacoustic signals corresponding to the respective positions on the sample are displayed on a display (e.g. a monitor television) 53 as image information. Now, the modulation frequency for the laser 21, which is a light source 1 for exciting the photoacoustic effect, will be explained. The transverse resolution of a photoacoustic signal is decided by the modulation frequency and the kind of a sample 170. Specifically, in the case where the excited light, beam is an ideal single beam and is also sufficiently converged, the resolution is given by the thermal diffusion length $\mu_s$ which is decided by the thermal property (thermal diffusion coefficient $\alpha$) of the sample 170 and the modulation frequency $f_r$ of the excited light beam as follows $$\mu_s = \sqrt{\frac{\alpha}{\pi f_r}} \quad (2)$$

For example, with the modulation frequency $f_r$ of 10 KHz.
for Si and Al, $\mu_s = 50$ $\mu$m,
for Al$_2$O$_3$, $\mu_s = 15$ $\mu$m, and
for SiO$_2$, $\mu_s = 5$ $\mu$m.
Conversely speaking, the modulation frequency is decided by required resolution and the kind of a sample.

In this embodiment, the modulated light beam irradiation optical system and the Michelson interferometer are constructed in a confocal optical system so that the transverse resolution of the photoacoustic signal can be enhanced, but the surface of the sample 170 must be coincident with the front focal point 131 of the objective lens 28. If not, the intermittent light beam from the laser 21 is not focused on the substrate surface so that the generated thermal distortion wave and so ultrasonic wave are very weak. Further, the light beam from the laser 31 is also not focused on the substrate surface so that the amount of the light passing through the pin-hole 40 is largely reduced and the obtained interference intensity becomes very weak. As a result, it becomes difficult to provide information relative to the surface and inside of the sample. However, by using this phenomenon conversely, an auto-focusing function with a very high accuracy can be added. This will be explained below.

Figure 9:
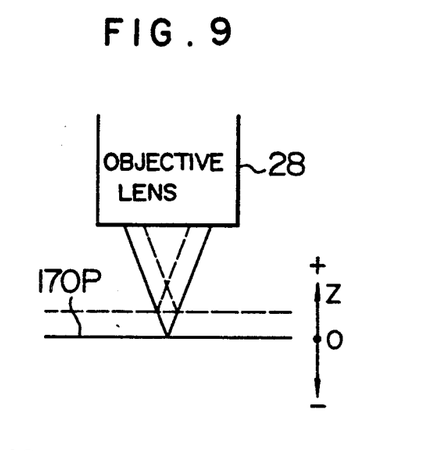
FIG. 9 is a view for explaining the operation in a z position relative to an auto-focusing system.
Figure 10:
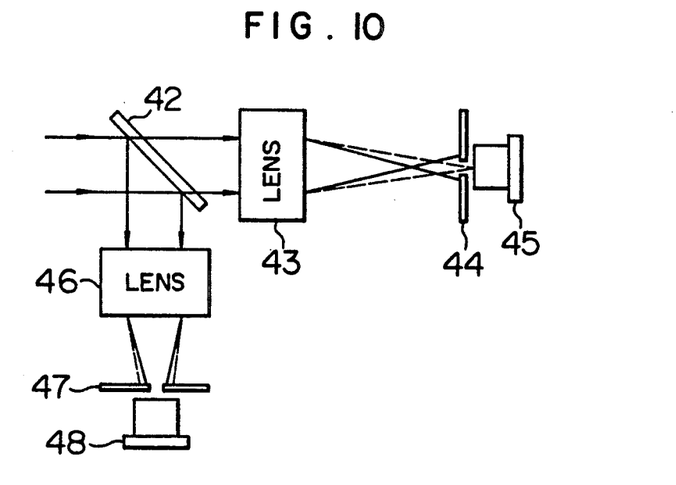
FIG. 10 is a view for explaining the operation of the auto-focusing system.
Figure 11:
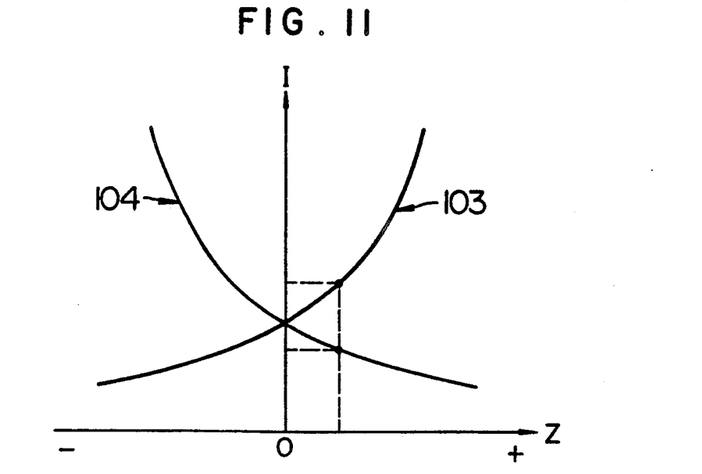
FIG. 11 is a graph showing the relation between the shifting amount of a Z stage and the output current of a photo-electric converting element.

The beam from the laser 31 reflected on the sample surface is branched or separated into two beams by the beam splitter 56, and one of them is further separated into two beams by a beam splitter 42, which are focused by lenses 43 and 46, respectively. Arranged on the respective light paths are photo-electric converting elements (e.g. photodiodes) 45 and 48 and further arranged are pin-holes 44 and 47 immediately therebefore. In this case, the photo-electric converting element 45 is located behind the rear focal point Fa of the lens 45 whereas the photo-converting element 48 is located before the rear focal point Fb of the lens 46. For convenience of explanation, it is now assumed that the objective lens 28 is chromatic-aberration-corrected for laser light and the laser light is focused on the surface of the sample 170. The position of the Z stage at this time is used as a reference position. If the Z stage rises to shift the sample surface 170P toward its plus side (broken line in FIG. 9), as indicated by the broken line in FIG. 10, the light amount passing through the pin-hole 44 is increased whereas the light amount passing through pin-hole 47 is decreased. FIG. 11 shows the relation between the shifting amount of Z stage and the respective output currents 103 and 104 from the photo-electric converting elements 45 and 48. By comparing both output currents in a comparator circuit 54 in FIG. 1, the position of Z stage 30 can be always monitored. In this case, the Z stage 30 is feedback-controlled so that the front focal point of 131 of the objective lens 28 always coincides with the surface of the sample 170. Incidentally, although the auto-focusing function mentioned above uses the modulated laser irradiation optical system 300, another laser irradiation optical system dedicated to the auto-focusing function may be provided independently.

Figure 5:
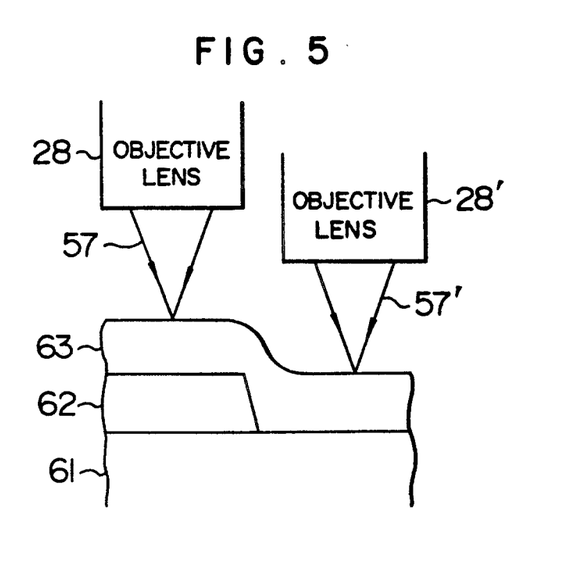
FIG. 5 is a view for explaining the focusing of a laser beam on the rugged surface of a sample.

In this way, the above auto-focusing function can be first realized by constructing the Michelson interferometer in a confocal optical system. Thus, even if the sample has a rugged surface as in a semiconductor wafer with a circuit pattern, stabilized laser beam can be always focused on the sample surface. In other words, the laser irradiation power to the sample surface can be always maintained constant. In FIG. 5, an SiO$_2$ layer 62 and a PSG (Phosphosilicate glass) layer are formed on a Si substrate 61, for example. In this embodiment, generally, the objective lens 28 is fixed and the Z stage is minutely shifted. However, sometimes, the Z stage is fixed and the objective lens 28 is minutely shifted.

In accordance with this embodiment, the modulated laser irradiation optical system 300 is constructed in a confocal optical system so that a minute beam spot free from the high order diffraction light component therearound can be focused on a sample whereby the transverse resolution and detection sensitivity of a photoacoustic signal can be improved. Further, the Michelson interferometer is also constructed in a confocal optical system so that an auto-focusing function with a high accuracy can be added. Namely, a stabilized laser beam can always be focused on a rugged sample surface whereby the photoacoustic signal, i.e. interference intensity signal can be improved in its transverse resolution, detection sensitivity and S/N.

Figure 6:
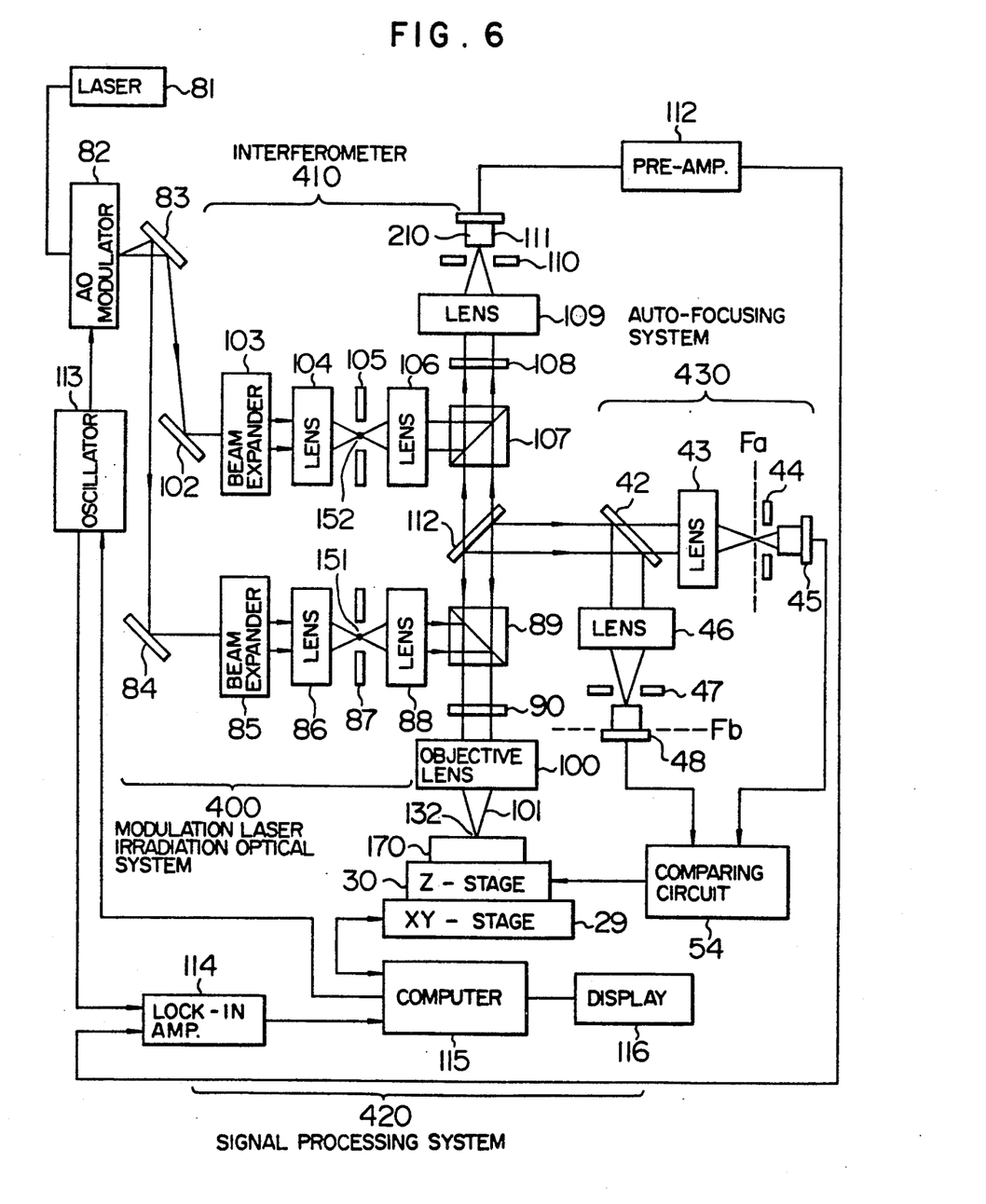
FIG. 6 is a block diagram showing the photo-acoustic signal detecting device (optical system) in accordance with a second embodiment of the present invention.

A second embodiment of the present invention will be explained. FIG. 6 shows the photoacoustic detecting optical system in accordance with a embodiment of the present invention in its block form. This optical system is composed of a modulated laser irradiation optical system 400, a heterodyne type Mach-Zehnder interferometer 410, a signal processing system 420 and auto-focusing system 430. In operation, an S polarized parallel light emitted from a laser 81 is intensity-modulated by an acoustic-electric modulation element 82 at a predetermined frequency and also separated into a zero order light and a first diffraction light. The zero order light is successively reflected on the mirrors 83 and 84. Further, it is expanded to a beam having a desired diameter by a beam expander 85, which is thereafter focused by a lens 86 to its rear focal point 151 thereof. A pin-hole 87, which is provided at the focal point 151, shades the high order diffraction light components 161a and 161b around the peak part 160 of the focused beam spot as shown in FIG. 2. As a result, the light intensity distribution immediately after having passed the pin-hole 87 provides only the peak part 160. Since the focal point 151 is also a front focal point of a lens 88, the light from the pin-hole 87, after having passed the lens 88, becomes an S polarized parallel light again.

This parallel light, after having been reflected on a polarized light beam splitter 89, passes through λ/4 plate 90 to become a circularly polarized light, which is a beam spot having the same light intensity distribution as shown in FIG. 3 again at a front focal point 132 of an objective lens 100, i.e. on a sample 170. Namely, the lens 88 and the objective lens 100 are in a confocal relation. A thermal distortion wave created at the focusing position 132 on the sample 170 generates an ultrasonic wave and also provides a minute displacement on sample surface.

Thus, the reflection light from the sample 170 contains this minute displacement as phase information. The reflection light passes through the objective lens 100 and λ/4 plate 90 to become a P polarized light, which permeates through the polarized light beam splitter 89 and another polarized light beam splitter 107.

On the other hand, the first order diffraction light, after having passed through the mirror 83 and a mirror 102, is expanded to a beam having a desired diameter by a beam expander 103, which is thereafter focused by a lens 104 to its rear focal point 152 thereof. A pin-hole 105, which is provided at the focal point 152, shades the high order diffraction light components 161a and 161b around the peak part 160 of the focused beam spot as shown in FIG. 2 in the same manner as mentioned above. As a result, the light intensity distribution immediately after having passed the pin-hole 105 provides only the peak part 160. Since the focal point 152 is also a front focal point of a lens 106, the light from the pin-hole 105, after having passed the lens 106, becomes an S polarized parallel light again. In FIG. 4, 120 represents the polarizing direction of the reflection light from the sample 170 and 121 represents that from the reference mirror 38. Since both reflection lights are orthogonal, they do not interfere with each other as they are. However, by inserting a polarization plate 108 into their optical path to place their polarization direction in a direction of 45 degrees, both reflection lights interfere with each other. The interference pattern thus formed, which includes the phase information relative to the minute displacement generated on the sample surface, is focused by a lens 109 at its rear focal point 210 and detected by a photo-electric converting element 111 such as a photodiode. Further, as in the first embodiment, a pin-hole 110 is arranged at the rear focal point 210 in order to shade the stray light created in the objective lens 100, the interference component created in a transparent film on the sample and the high order diffraction light component create due to the minute rugged sample surface.

As understood from the above explanation, in the heterodyne type Mach-Zehender interferometer in this embodiment, the 106, the objective lens 100 and the lens 109 are in a confocal relation. Assuming that the output of a laser is I, the photo-electric converted interference intensity signal is $I_D$ can be expressed by $$I_D = I_R + I_S + 2\sqrt{I_R}\sqrt{I_S}\cos\{2\pi f_B t - 4\pi\delta(t)/ + \phi(t)\} \quad (3)$$

where $I_R$ is the intensity of the first order diffraction light reflected by the beam splitter 107, $I_S$ is the intensity of the light reflected on the sample 170 and permeated through the polarized light beam splitter 107, $f_B$ is the modulation frequency of the photoacoustic modulation element 82, $\delta(t)$ (=A cos $2\pi f_u t$) is the minute displacement on the sample 170, A is a constant peculiar to the substance of the sample, $f_U$ is the frequency of the ultrasonic wave generated in the sample 170, $\phi(t)$ is the phase due to the light path difference in the interferometer, and λ is the oscillation frequency of the laser 81.

The interference intensity signal $I_D$ is amplified by a pre-amplifier 112 and thereafter sent to a lock-in amplifier 114. The lock-in amplifier 114, using as a reference signal a modulated frequency signal from an oscillator 113 used for driving the acoustic-optical modulation element 82, extracts the modulated frequency component $\delta(t)$ and phase component contained in the interference intensity signal. The frequency component and the phase component have information relative to the surface or inside of the sample according to the frequency. Therefore, if there is a defect such as a crack inside the sample, the modulated frequency component in the interference intensity signal provides a signal change so that the presence of the defect can be noticed. A shifting signal for an XY stage 29 and an output signal from the lock-in amplifier 114 are processed by a computer 115. Accordingly, the photoacoustic signals corresponding to the respective positions on the sample are displayed on a display (e.g. a monitor television) 116 as image information.

An auto-focusing system 430 in this embodiment is the same as that in the first embodiment shown in FIG. 1 in their construction and function and so explanation therefor will be omitted.

In accordance with this embodiment, as in the first embodiment, the modulated laser irradiation optical system 400 is constructed in a confocal optical system so that a minute beam spot free from the high order diffraction light component on its periphery can be focused on a sample whereby the transverse resolution and detection sensitivity of a photoacoustic signal can be improved. Further, the Mach-Zehender interferometer is also constructed in a confocal optical system so that an auto-focusing function with a high accuracy can be added. Namely, a stabilized laser beam can always be focused on a rugged sample surface whereby the photoacoustic signal, i.e. interference intensity signal can be improved in its transverse resolution, detection sensitivity and S/N. Moreover, this embodiment has advantages that the construction of the optical systems is simplified since only one laser is employed and that it is resistant to external disturbance such as vibration since the adopted Mach-Zehender interferometer does not use a reference mirror.

Accordingly, in accordance with the present invention, both the modulated laser irradiation optical system and the interferometer are constructed as confocal optical systems so that the photoacoustic signal can be improved in its transverse resolution, detecting sensitivity and S/N, and also the present invention can be applied to a sample with a rugged surface, thus permitting information relative to the surface and inside of the sample to be measured with a high accuracy.

Incidentally, although in the above explanation about the present invention, a laser was used as a light source for photoacoustic effect excitation and for detection, the other light source such as a mercury lamp may be used.

We claim:

1. An apparatus for detecting information relative to a surface of sub-surface of a sample using a photoacoustic effect, the apparatus comprising:
   an excitation light source means for emitting an excitation light;
   an acoustic-optical modulation means for intensity modulating the excitation light emitted from the excitation light source means at a predetermined frequency;
   focusing means to focus said intensity-modulated excitation light onto the sample surface thereby generating a thermal distortion due to a photoacoustic effect, said focusing means comprising a first confocal optical means to converge said intensity-modulated excitation light into a fine intensity-modulated excitation light spot on the sample surface and first removing means for removing high order diffraction light components around said fine intensity-modulated excitation light spot;
   light interference detection means for detecting an interference intensity signal caused by said generated thermal distortion, said light interference detection means comprising an interference light source means for emitting an interference light, a second confocal optical means for irradiating the sample surface by converging the interference light into a fine interference light spot whereby the fine interference light spot and the intensity-modulated excitation fine light spot substantially occupy the same sample surface position, second removing means for removing high order diffraction light components around said fine interference light spot, and an optical detection means for detecting a focused interfered light that is reflected from the irradiated sample surface and which contains the interference intensity signal, said optical detection means including a third removing means for removing high order light diffraction components from the focused interfered light; and,
   detecting means for detecting said information relative to either the sample surface or sub-surface in accordance with a modulated frequency component contained in the interference intensity signal, said detecting means containing an extracting means for extracting said modulated frequency component contained in said interference intensity signal detected by said light interference detection means, said extraction means using said predetermined modulating frequency of said acoustic-optical modulation means as a reference.

2. The apparatus according to claim 1, wherein said first removing means includes a first pin-hole for removing the high order diffraction light components around the fine intensity-modulated excitation light spot.

3. The apparatus according to claim 1, wherein said second removing means includes a second pin-hole for removing high order diffraction light components around the interference light spot.

4. The apparatus according to claim 1, wherein said light interference detection means comprises:
   a photo-electric converting element for detecting an interference light containing information relative to the thermal distortion in said sample; and
   wherein said second removing means includes a second pin-hole, for removing high order diffraction light components around the fine interference light spot.

5. The apparatus according to claim 1, wherein said focusing means comprises:
   the first removing means comprising a plurality of lenses in confocal relation;
   a first pin-hole, arranged at the confocal point of said plurality of lenses, for removing high order diffraction light components around the fine intensity-modulated excitation light spot; and
   an objective lens for focusing on said sample the intensity modulated excitation light, the high order diffraction light components of which has been removed by said first pin-hole,
   said light interference detection means comprises:
   the second removing means comprising a plurality of lenses in a confocal relation;
   a second pin-hole, arranged at the confocal point of said plurality of lenses, for removing high order diffraction light components around the fine interference light spot;
   a beam splitter for separating the interference light from said interference light source into a first and second light beam, said first light beam is used as a reference light, the second light beam is focused and reflected on said sample and contains information relative to the thermal distortion of the sample due to photoacoustic effect;
   a polarizing plate for polarizing the first and second light beams; and
   a photo-electric converting element for detecting an interference light of said first and second light beams which have permeated through said polarizing plate.

6. The apparatus according to claim 1, further comprising an auto-focusing adjusting means which includes two photo-electric converting elements for detecting the light reflected from said sample and, by comparing detection currents from said two photo-electric converting elements, adjusts a position of said focusing means or of said sample so that a diameter of the fine intensity-modulated excitation light spot formed on the sample by said focusing means is always constant.

7. The apparatus according to claim 1, further comprising an auto-focusing adjusting means which comprises:
   a Z stage for adjusting the vertical position of said sample;

a first beam splitter for separating the intensity-modulated excitation light into a first and second light beam;

a second beam splitter for further separating the first light beam into a third and fifth light beam;

a first lens for focusing the first light beam from said second beam splitter;

a first photo-electric converting element which is located behind the rear focal point of said first lens;

a second lens for focusing the fifth light beam from said second beam splitter;

a second photo-electric converting element which is located before the rear focal point of said second lens; and a comparing circuit for comparing a first and second current detected by said first and second photo-electric converting elements respectively whereby a position of said focusing means or of said sample is adjusted in accordance with said comparison so that a diameter of the fine intensity-modulated excitation light spot formed on said sample by said focusing means is always constant.

8. The apparatus according to claim 7, further comprising a light source dedicated to auto-focusing and which is separate from the interference light source.

9. The apparatus according to claim 1, wherein said interference light source and said intensity-modulated excitation light source are lasers.

10. The apparatus according to claim 1, wherein said interference light source and said intensity-modulated light source are mercury lamps.

11. The apparatus according to claim 1, wherein said modulation means is an acoustic-optical modulation element.

12. The apparatus according to claim 1, wherein said modulation means modulates the intensity-modulated excitation light emitted from said light source and also separates it into a zero order light and a first order diffraction light;

first pin-holes included in said first removing means removes high order diffraction light components around light spots of said zero order light and said first order diffraction light;

said focusing means focuses and irradiates said zero order light on the sample, wherein said zero order light is reflected from the sample and contains information relative to the thermal distortion of the sample created by the photoacoustic effect; and said light interference detection means causes said first diffraction light and said zero order light to interfere to detect a resultant interference light, thereby detecting said thermal distortion of the sample.

13. An apparatus for detecting information relative to a surface or subsurface of a sample using a photoacoustic effect comprising:

an excitation light source means for emitting an excitation light;

an acoustic-optical modulation means for intensity-modulating the excitation light emitted from said excitation light source means at a predetermined frequency;

focusing means for focusing said intensity-modulated excitation light onto a sample surface thereby generating a thermal distortion due to a photoacoustic effect, said focusing means comprising a first confocal optical means to converge said intensity-modulated excitation light into a fine intensity-modulated exciting light spot on the sample surface, and first removing means for removing high order diffraction light components around said fine intensity-modulated excitation light spot;

light interference detection means for detecting an interference intensity signal caused by said generated thermal distortion, said light interference detection means comprising an interference light source means for emitting an interference light;

a second confocal optical means for irradiating the sample surface by converging the interference light spot whereby the fine interference light spot and the intensity-modulated excitation fine light spot substantially occupy the same sample surface, second removing means for removing high order diffraction light components around said interference light spot, and an optical detection means for detecting a focused interfered light that is reflected from the irradiated sample surface and which contains the interference intensity signal, said optical detection means including a third removing means for removing high order light diffraction components from the focused interfered light;

detecting means for detecting said information relative to the sample surface or sub-surface in accordance with a modulated frequency component contained in the interference intensity signal, said detecting means containing an extracting means for extracting said modulated frequency component contained in said interference intensity signal detected by said light interference detection means, said extraction means using said predetermined modulating frequency of said acoustic-optical modulation means as a reference; and, auto-focusing adjusting means for adjusting said focusing means so that said fine intensity-modulated excitation light spot obtained by the focusing means is focused correctly on said sample.

14. The apparatus according to claim 13, wherein said focusing means comprises:

a first lens for focusing said intensity-modulated excitation light at a rear focal point thereof, a first pin-hole located at said rear focal point of the first lens, a second lens for changing the intensity-modulated excitation light having passed through said first pin-hole into a parallel intensity-modulated excitation light, and an objective lens, in confocal relation with said second lens, for focusing said intensity-modulated excitation light onto the sample; and, said light interference detection means comprises:

a third lens for focusing said interference light at a rear focal point thereof, a second pin-hole located at said rear focal point of the third lens, a fourth lens for changing the interference light having passed through said second pin-hole into parallel interference light, a polarization plate for polarizing said interference light having passed through said fourth lens and said focused interfered light having been reflected from the sample and containing an information relative to the thermal distortion in the sample due to photoacoustic effect, and a photo-electric converting element for detecting an interference light of said focused interfered light and said polarized interference light which have passed through said polarization plate.

* * * * *

UNITED STATES PATENT AND TRADEMARK OFFICE
CERTIFICATE OF CORRECTION

PATENT NO. : 5,083,869

DATED : January 28, 1992

INVENTOR(S) : Toshihiko Nakata, et al.

It is certified that error appears in the above-identified patent and that said Letters Patent is hereby corrected as shown below:

In the Title: Delete "PHOTOCOUSTIC" and substitute therefor --PHOTOACOUSTIC--.

Claim 1, column 9, line 21, after "a surface" delete "of" and substitute therefor --or--.

Signed and Sealed this

Twentieth Day of April, 1993

*Attest:*

MICHAEL K. KIRK

*Attesting Officer*       *Acting Commissioner of Patents and Trademarks*